United States Patent [19]

Schultz et al.

[11] 3,970,435

[45] July 20, 1976

[54] APPARATUS AND METHOD FOR METHANATION

[75] Inventors: Thomas J. Schultz, Toledo; Klaus H. Hemsath, Sylvania, both of Ohio

[73] Assignee: Midland-Ross Corporation, Cleveland, Ohio

[22] Filed: Mar. 27, 1975

[21] Appl. No.: 562,796

[52] U.S. Cl. .............................. 48/61; 23/288 R; 48/86 A; 48/197 R; 260/449 M
[51] Int. Cl.² ........................... B10J 7/00; C10J 1/00
[58] Field of Search ................. 48/61, 86 A, 197 R; 260/449 M; 23/288 R; 252/373

[56] References Cited
UNITED STATES PATENTS

| | | | |
|---|---|---|---|
| 2,778,610 | 1/1957 | Bruegger ........................... | 23/288 R |
| 3,002,816 | 10/1961 | Friend et al. ...................... | 23/288 K |
| 3,511,624 | 5/1970 | Humphries et al. ................ | 48/197 R |

*Primary Examiner*—Robert L. Lindsay, Jr.
*Assistant Examiner*—George C. Yeung
*Attorney, Agent, or Firm*—Frank J. Nawalanic

[57] ABSTRACT

An improved process and apparatus for upgrading coal gas to methane is provided by a simple and efficient methanator comprising an open-ended enclosure submersed within a liquid bath and carrying a catalytic insert having increasing degrees of controlled reactivity which the said gas contacts as the gas travels through the enclosure. In the presence of the catalyst, heat is generated from the methanation reaction at a controlled rate and substantially dissipated by the liquid bath so that substantially all the gaseous reductants, CO and $H_2$, are reacted to methane at a relatively low controlled temperature.

9 Claims, 4 Drawing Figures

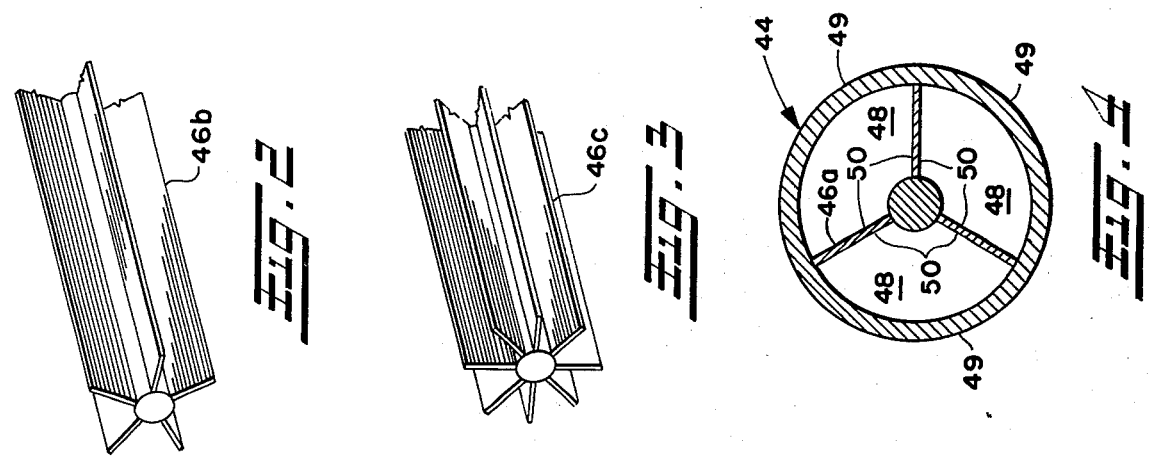
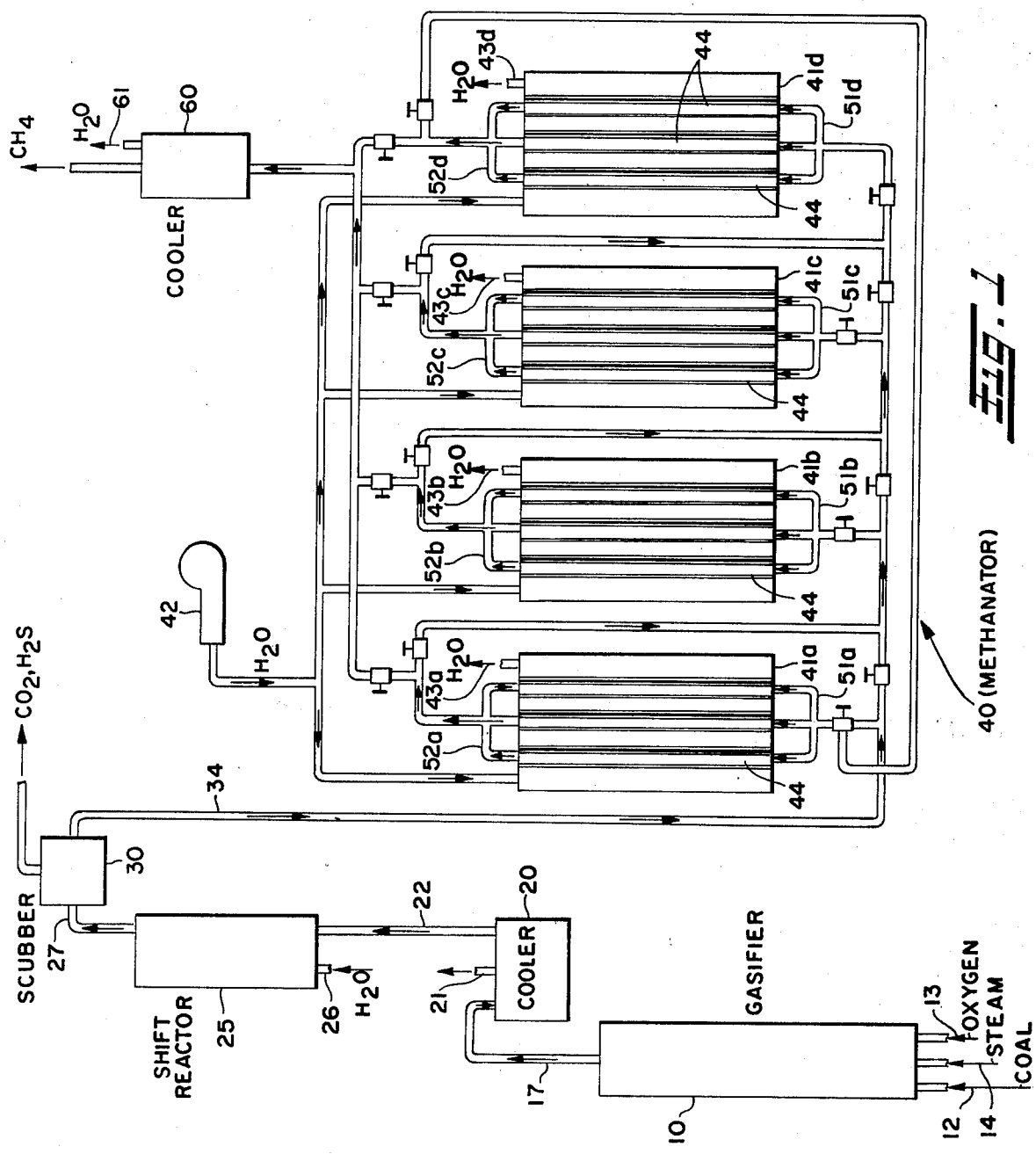

APPARATUS AND METHOD FOR METHANATION

This invention relates generally to an improvement in the art of manufacturing synthetic gas and, more particularly, to a catalytic reaction chamber wherein gases are exothermically reacted to produce the synthetic gas.

The invention is particularly applicable to the production of synthetic methane gas from coal in sufficient quality and quantity suitable for pumping into pipelines for commercial and residential heating and will thus be described with particular reference thereto. However, it will be appreciated by those skilled in the art that the invention may have broader applications and may be used in any process where gases are to be exothermically reacted in a controlled manner to a preferred equilibrium condition.

Heretofore, synthetic methane gas has been commercially produced from liquid hydrocarbon feed stock. When the stock is gasified a relatively low percentage of reducing gases, CO and $H_2$, are formed. These reducing gases are shifted into a proper reaction ratio and then reacted in a methanator. Commercially available methanators suitable for reacting the reductants produced from liquid feed stock generally consist of packed bed catalysts that use cooled recycled product gas to remove the heat from the beds.

The removal of heat is essential to the efficient operation of the methanator. That is, the methane reaction

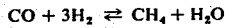
$$CO + 3H_2 \rightleftarrows CH_4 + H_2O$$

is reversible and when shifted to the right to produce methane is exothermic. Accordingly, a catalyst must be employed to allow the reaction to proceed to equilibrium at the lowest possible temperature to produce a product gas high in methane concentration. That is, the heat released by the methane reaction raises the temperature of the gases and this heat must be removed to permit the reaction to progress at preferred, relatively low temperatures.

In particular, when coal is gasified it produces a lower percentage of methane and higher percentages of reducing gas than that which results when the feed stock is liquid hydrocarbon. The increase in reductant percentage of the feed gas results in liberation of greater quantities of heat from the methane reaction which would either destroy the catalyst in a packed bed or necessitate the use of economically unfeasible cooling arrangements in the packed bed.

Other known methanator concepts include catalytically coated heat exchanger tubes, slurry catalyst and fluidized catalyst beds, each of which, as presently developed, possesses inherent disadvantages in their operation and/or construction which render them unsuitable for methanating a coal-gasified fed gas. Inherent problems in the slurry catalyst and fluidized bed catalyst concepts occur with respect to the attrition and elutriation of the catalyst and the resulting problems with separating the fines from the carrier fluids. Catalytic heat exchange tubes to which this invention is directed can only be manufactured in relatively short lengths due to the required catalyst application techniques. Importantly, these tubes are designed to provide cooling for the highest reaction rates occurring at the tube inlet. Accordingly, the reaction rates and heat release rates continue to decline as the gases travel through the length of the tubes. Therefore, the conversion rate per unit area of the tubes decreases along the tube resulting in excessively long tubes which cannot be commercially produced with today's coating techniques, or, alternatively, an excessive quantity of reaction tubes would be required thereby rendering the approach commercially unfeasible. Any attempt to reduce the tube length or number would result in a product gas having an unsatisfactory methane percentage.

It is thus an object of the subject invention to provide a methanator of the heat exchange type where the catalyst activity within the heat exchanger is varied in accordance with the reductant concentration at any point within the heat exchanger to produce a controlled methane reaction which liberates heat at approximately the same rate that the heat can be removed from the heat exchanger by a cooling medium in contact therewith.

This object along with other features of the invention is achieved by providing a longitudinally elongated, open-ended enclosure with an insert coated with a common catalyst such as nickel positioned therein. The enclosure is submersed in a liquid bath containing a cooling medium and feed gas is pumped into the enclosure at one end thereof, reacted within the enclosure in the presence of the catalytic insert as the gas travels the length of the enclosure and exits the enclosure at the opposite end in the form of methane gas and water vapor. The degree of reactivity of the catalyst within the enclosure is progressively varied as a function of the heat generated by the methane reaction which, in turn, is dependent upon the feed gas makeup, mass flow rate and temperature at any point along the length of the enclosure. Since the cooling capacity of the enclosure is constant along the entire length thereof, the activity of the catalyst is varied to generate approximately the same quantity of heat value resulting from the methane reaction which is then sized or matched to the cooling capacity of the enclosure. In this manner, the methane reaction is permitted to approach equilibrium at a relatively low temperature which does not destroy the catalyst while resulting in a product gas of relatively high methane concentration.

Another feature of the subject invention resides in its ability to function continuously in a large gas generation plant. In such environment, the enclosure takes the form of three (or more) banks of heat exchange tubes submersed in a cooling medium (methanation vats) and connected in series. In each tube in the first bank a catalytic insert having a predetermined first degree of reactivity is provided. In each tube in the second bank a catalytic insert having a higher degree of reactivity is provided and in the third bank a catalytic insert having a still higher predetermined degree of reactivity is provided. The methane reaction occurs at a generally constant temperature in each tube in each bank and the tubes are sized and designed so that by the time the feed gas travels from the first to the second to the third bank of tubes, equilibrium has been substantially reached and a product gas high in methane is produced. As a function of time, the reactivity of all the catalytic inserts in all the banks will decrease until the product gas reaches an unacceptable composition. At this point, a fourth bank of reaction tubes having catalytic inserts with the same degree of reactivity as initially the third bank had may be valved into the system in place of the third bank with the first bank being valved out of the system for repair or catalyst regeneration; the feed gas continuously traveling from the second through the third and the fourth banks. Alternatively, extra tubes in each bank may be provided with the valving shifting the feed gas from one set of tubes within one bank to the other set of tubes in the same bank which have fresh or new catalytic inserts.

In accordance with a more specific feature of the subject invention, the heat transfer relationship existing between the heat generated within the enclosure or tube and the cooling medium surrounding the enclosure is maintained in a uniform manner by means of catalytic inserts. Such inserts divide the interior cross section of the enclosure into a plurality of longitudinally elongated ducts. Each duct has a cross-sectional configuration defined as including a cross-sectional segment of the wall of the enclosure and a cross-sectional segment of the catalytic insert. The ratio of the areas of the wall segment and insert segment are substantially equal for all the ducts. In this manner, the feed gas flow through each reaction tube is subdivided into mass flows and each mass unit of flow in all of the ducts is exposed to the same catalytic or heat generating area and the same wall or cooling area.

In accordance with yet another specific feature of the invention, the heat exchange enclosure is sized so as not to produce a significant pressure drop in the gases flowing therethrough. This enables the gases to flow through the entire gasification plant under a pressure produced only by the combustion of the feed stock in the gasifier and therefore eliminates the need for additional gas compression equipment in the process and also recycle compressors within the methanator which function to control the gas temperature, heretofore required in gasification plants. Resultant savings on equipment and operating costs for the plant are substantial.

The invention may take physiical form in certain parts and arrangement of parts, a preferred embodiment of which will be described in detail herein and illustrated in accompanying drawings which form a part hereof and wherein:

FIG. 1 is a schematic illustration of a coal methanation plant employing the methanator of the subject invention;

FIGS. 2 and 3 show various designs of catalytic inserts; and

FIG. 4 shows in cross section still another catalytic insert design placed within a heat exchange tube.

Referring now to the drawings wherein the showings are for the purpose of illustrating a preferred embodiment of the invention only and not for the purpose of limiting same, FIG. 1 illustrates in diagrammatic form, a process for producing synthetic methane gas from coal. "Coal" as used herein means a combustible substance of organic origin and includes such materials commonly referred to as peat, lignite, bituminous (soft coal) and anthracite (hard coal). The component parts generally shown in FIG. 1 include a gasifier 10, a first cooler 20, a shift reactor 25, an acid gas scrubber 30, a methanation reactor 40 and a second cooler 60. All the component parts illustrated with the exception of methanator 40 are individually and by themselves believed to be known in various arts and thus are not shown or described in detail herein.

METHANATION PLANT

The gasifier facility 10 illustrated is of the solid type (although the invention will function with liquid type gasifiers) which mixes in a known combustible manner coal from line 12, oxygen from line 13, and steam from line 14 to produce a raw feed gas. Feeding gasifier 10 with a typical strain of bituminous coal will produce a typical raw feed gas exiting gasifier 10 through line 17 comprising generally 35% $H_2$, 35% CO, 2% $CO_2$, 2% $H_2O$, 25% $CH_4$, and 1% impuritiies such as $H_2S$, flyash and tars. Gasifier 10 is normally operated at an elevated pressure (typically 1,000 psig) so that pressure of the raw feed gas in line 17 is sufficient to meet operational requirements of all the components (first cooler 20, shift reactor 25, acid gas scrubber 30, methanation reactor 40, second cooler 60) of the gasification process without additional compression. It should be noted that gasification of coal produces a raw feed gas, characterized by having reductants, $H_2$ and CO, comprising at least 50% of the gas composition. In contrast, gasification of liquid hydrocarbon feed stock will produce a raw feed gas typically comprising a reductant gas comprising 35% of the raw feed gas.

The raw feed gas is transmitted through line 17 to a cooler 20 where the impurities, flyash and tars, are separated and exit via line 21. The feed gas leaving cooler 20 in line 22 is generally at a temperature of 750°F.

Since the reducing gases, CO and $H_2$, in the feed gases are not necessarily in their proper proportions to completely react with one another to produce methane, the feed gases in line 22 are fed into a shift reactor 25. The feed gases within shift reactor 25 are mixed with steam from line 26 at a elevated temperature of approximately 500°F. to vary the $H_2$-CO proportions in accordance with the known reversible equation

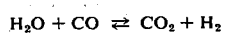

$$H_2O + CO \rightleftarrows CO_2 + H_2$$

The shift reaction can be controlled by gas analyzer probes (not shown) in the line upstream and/or downstream of shift reactor 25.

The feed gas exits shift reactor 25 through line 27 and enters an acid gas scrubber 30 where the feed gases are further refined by removing the gases, $CO_2$ and $H_2S$. The feed gas leaves gas scrubber 30 in a refined state, generally comprising 18.8% CO, 56.2% $H_2$ and 25% $CH_4$, through line 34 and enters methanation reactor 40. In methanator 40, the reducing gases or reductants will react in accordance with the reversible equation

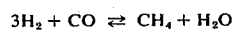

$$3H_2 + CO \rightleftarrows CH_4 + H_2O$$

to produce methane. When the reaction is to the right to produce methane, the reaction is exothermic and the methanation reactor of the subject invention is designed to permit the reaction to proceed towards the right at a relatively low equilibrium temperature to produce a high methane gas with water vapor. The water vapor is then condensed in cooler 60 and removed from the cooler as condensate in line 61.

METHANATOR

Methanation reactor 40 comprises a plurality of vats 41a, 41b, 41c, 41d, any three of which are progressively linked in series. That is, methanator vats 41a, 41b, 41c or 41b, 41c, 41d or 41c, 41d, 41a, etc., may be progressively connected in the seriies relationships indicated.

Each methanator vat is filled with a cooling liquid medium under pressure. It is contemplated that water will function as an excellent cooling medium and may be supplied to each vat by a common pump 42 generating a water pressure within each vat at approximately 1,000 psig. Heat from the methane reaction will generate steam in each vat which exits vats 41a, 41b, 41c, 41d through lines 43a, 43b, 43c, 43d respectively. (Other high temperature heat transfer fluids may also be employed for cooling.) In startup situations, the liquid cooling medium may be heated externally of the vats and pumped in a hot state into vat enclosures 41a, 41b, 41c, or each vat may include means for heating the liquid therein to a predetermined startup temperature.

A predetermined plurality of relatively small diameter reaction tubes (or heat exchange enclosures) 44 are inserted in methanator vats 41a, 41b, 41c, 41d. It is contemplated for the feed gas composition indicated that each reaction tube will be constructed of a good heat conductive material such as steel and will be approximately 2 inches in I.D. with a wall thickness of approximately 0.25 inch.

Each tube 44 contains an insert 46 which is catalytically coated in a known manner with any type of common catalyst, e.g., nickel, cobalt, ruthenium, preferably nickel. The reactivity of each catalytic insert 46 is matched in series relationship to methanator vats 41. That is, catalytic inserts having a first predetermined degree of reactivity and identified as 46a are inserted in those tubes submersed within first methanator vat 41a. Likewise, catalytic inserts having a second degree of reactivity 46b which is higher than that of first catalytic inserts 46a are inserted within reaction tubes 44 placed in second methanator vat 41b. Catalytic inserts having a third degree of reactivity 46c higher than that of second catalytic inserts 46b are inserted within reaction tubes 44 within third methanator vat 41c and fourth methanator vat 41d.

The reactivity rate of catalytic inserts 46 may be accurately controlled and sized by the catalytic insert shape. Such catalytic insert shapes may assume a finned construction as shown in FIGS. 2, 3 and 4 when tubular reaction tubes 44 are employed. Suitable fastening means can be employed to suspend each insert 46 within its reaction tube 44 or the insert 46 can be sized closely to the dimension of reaction tube 44 to support itself therein. Other heat exchange enclosure configurations may dictate use of differently shaped catalytic inserts. As shown in FIG. 4, a three finned insert 46a for use within reaction tubes 44 in first methanator vat 41a is employed. A five finned catalytic insert 46b as shown in FIG. 2 is used in reaction tubes 44 within second methanator vat 41b and in FIG. 3 an eight finned catalytic inert 46c is employed in reaction tubes 44 for use in methanator vats 41c and 41d. Since the refined feed gas flows through reaction tubes in contact with the catalytic inserts, increasing the area of the catalytic inserts is one way of progressively increasing the degree of reactivity of the catalyst in methanator vats 41a, 41b, 41c, connected in series relationship, Whatever type of catalytic insert 46 is employed in reaction tube 44, it is necessary for proper heat transfer considerations that the insert divide the interior of the reaction tube or heat exchange enclosure 44 into ducts 48 with a portion of the duct cross-sectional periphery or configuration embodying or including a segment 49 of the tube wall (FIG. 4) and a segment 50 of the insert 46. More particularly, ducts 48 subdivide the total feed gas flow through each reaction tube 44 into several different masses all flowing at approximately the same velocity. The ducts are sized so that each mass flow, expressed in units of mass, contacts a constant portion of the catalyst (i.e., units of mass flow/catalytic units of area) and each unit of mass flow is exposed to a constant portion of the periphery of the enclosure (i.e., units of mass flow/enclosure units of area). Thus any configuration of insert 46 should be acceptable if each duct formed in each tube 44 has the same ratio of catalytic segment area 50 to wall segment 49 as the other ducts 48 in the same reaction tube. In the embodiment shown, each duct area is equal and each unit mass flow of feed gas within reaction tube 44 will be exposed to a constant catalytic area thereby developing a constant unit of heat from the metane reaction which in turn will be uniformly dissipated by the cooling medium because of the constant unit of tube wall area to which the heat is exposed. Other configurations will suggest themselves to those skilled in the art. In this connection, it should be noted that each duct's cross-sectional size is maintained at a value which does not produce any significant pressure drop in gas flowing therethrough (approximately constant flow) and for this reason the methanation reactor 40 of the subject invention can still function at gas pressures as low as 5 psig.

METHANATOR OPERATION

Feed gas from line 34 of a typical gas composition comprising 18.8% CO, 56.2% $H_2$ and 25% $CH_4$ is fed into first methanator vat 41a by a bustle or octopus feed pipe arrangement 51a which directs a uniform flow of feed gas through each reactor tube 44 in first methanator vat 41a. By controlling the length of the reaction tube, the degree of reactivity of catalytic insert 46 within the tube, the size of the tube, etc., the methane reaction can be controlled within first methanator vat 41a to produce a reaction which would generate an amount of heat which will be dissipated by radiation and convection into the cooling medium. Therefore, the degree of reactivity of first catalytic insert 46a can be determined so that the heat of the feed gases does not appreciably rise in value from the inlet end of the reaction tube to the outlet end of the reaction tube. In particular, the heat released from the methane reaction can be controlled via the dissipation effects of the liquid cooling medium so that a temperature within the reaction tube (typically 900°F. or above) which would destroy the catalytic coating is not attained. In the embodiment illustrated in FIG. 1, the temperature of the refined feed gas entering the reaction tubes of first methanator 41a would be at approximately 500°F. and the gas leaving the outlet end of the reaction tubes in first methanator 41a through the outlet bustle feed arrangement 52a would be approximately 750°F. Within each reaction tube in first methanator vat 41a, the feed gases (but for the cooling medium) would rise in temperature from approximately 500°F. to approximately 1500°F. but the cooling liquid medium would reduce this temperature to the outlet temperature of 750°F. as the gases travel through the tubes. It should be clear to those skilled in the art that the relatively low degree of catalytic reactivity of first catalytic inserts 46a tends to result in a methane reaction condition occurring at the outlet end of the reaction tubes in first methanator vat 41a which produces or increases the methane composition of the gas to a value which is not commercially satisfactory. That is, the composition of the partly reacted refined feed gas leaving outlet bustle feed arrangement 52a from the first methanator vat is approximately 42.7% $H_2$, 14.3% CO, 7.2% $H_2O$, 35.8% $CH_4$. (On the other hand, if gasifier 10 were charged with liquid hydrocarbon feed stock, the relatively low percentage of reductant gases produced in the gasifier may possibly be reacted to an equilibrium condition in one methanator vat which would produce a commerically acceptable percentage of methane gas.) It is for this reason that the partially reacted refined feed gas is fed into a second methanator vat 41b which has a higher degree of catalytic activity than first methanator vat 41a. The degree of reactivity of catalytic insert 46b in second methanator vat 41b is likewise determined as a function of the heat released from the methane reaction therein which is matched or sized to the heat value which can be dissipated by the liquid cooling medium in the second vat. The partially refined gases would enter second inlet bustle feed arrangement 51b at a typical temperature of 750°F. and leave second outlet bustle feed arrangement 52b at a typical temperature of 750°. A further methane reaction will occur in the feed gas and second methanator vat 41b and typically will produce a partially-reacted, refined feed composition of 24.8% $H_2$, 8.3% CO, 16.8% $H_2$), 50.1% $CH_4$ leaving the outlet bustle feed arrangment 52b of second methanator vat 41b. By subjecting this gas to a final methane reaction temperature in the presence of third catalytic insert 46c having a high degree of reactivity (inlet temperature typically at 750°F. and outlet temperature typically at 750°F), a product gas is produced which, after condensing the water vapor therefrom, results in a substantially pure (98.5% composition) methane gas. In this sense, it should be noted that natural gas used in industrial and home heating comprises 88–90% methane and some industrial heat applications can function with less methane. Accordingly, the invention may function, in such instances, with only two methanator vats.

As a function of time, the reactivity of catalytic inserts 46 will begin to decrease. Eventually, the reactivity will decrease to a point where the purity of the product gas will be adversely affected. One operation that can be employed in methanation reactor 40 to compensate for the reduced reactivity of the catalytic inserts would be to provide an extra number of reaction tubes 44 in each methanator vat 41 and provide valving in bustle feed arrangement 51, 52 whereby certain tubes could be moved into and out of each methanator vat permitting replacement of the catalytic inserts within the removed reaction tubes which were valved out of operation in each vat.

Another approach is diagrammatically illustrated in FIG. 1. In this arrangement, an extra methanator vat 41d is provided and catalytic inserts of the highest degree of reactivity 46c are inserted within reaction tubes 44 in fourth methanator vat 41d. When the degree of reactivity of methanator vats 41a, 41b, 41c decreases to a point of producing unacceptable product gas, suitable valving as shown in FIG. 1 may be employed to permit first methanator vat 41a to be valved out of the system, and methanator vats 41b, 41c, 41d to be valved into the system in that sequence. When the product gas produced by the second series of methanator vats 41b, 41c, 41d begins to slip in quality, first methanator vat 41a which now has been equipped with catalytic inserts of the highest degree of reactivity 46c in its reaction tubes is valved into sequence as the last methanator vat in the arrangement which reacts the feed gas in the vat series 41c, 41d, 41a. The catalytic inserts 46b in second methanator vat 41b are then removed and catalytic inserts 46c are inserted therein for the cycle to continue. It sould be clear that when the vats are sequenced in this manner, that eventually, all the vats will have the same catalytic insert shapes, but because the catalysts have been poisoned, in varying degrees, the reactivity will nevertheless remain progressively increased.

CALCULATIONS

The following calculations are illustrative of the technique used to design the methanator 40 of the subject invention for a typical 250 MM (million) SCFD (standard cubic feet per day) SNG (synthetic natural gas) plant.

As a typical example, a series of 2 inches I.D. reaction tubes 44 (which diameter will result in negligible pressure drop of gases flowing therethrough) and a cooling medium of boiling water (550°F) at 1,000 psig are chosen. A 250 MM SCFD plant will require a gas flow rate of approximately 700,000 lbs./hour. Assuming a feed gas composition of 25% $CH_4$, 18.7% CO and 56.3% $H_2$, known reaction curves indicate that approximately 920,000 BTU/hour will be liberated from the methane reaction if same occurs at a temperature of approximately 850°F. A typical methanator, designed so that the catalyst operates at its maximum temperature (approximately 850°F can produce about 1470 SCFD (at equilibrium) product gas per square foot of contact surface. The reaction tubes 44 are typically designed for 30,000 lb./hr. ft.$^2$ mass flow rate therethrough which in turn will result in a connection heat transfer coefficient of about 65 BTU/hr. ft.$^2$ °F.

Methanator Tube Design

The total cross-sectional flow area through each vat will be 700,000 lb./hr. ÷ 30,000 lb./hr. ft.= 23.3 ft.$^2$. If 75% of the tube area is open to flow (the remaining 25% to be taken up by the catalytic insert), there will be 1430 tubes in each vat.

If the temperature differential between the gas within the reaction tube and the cooling medium is 200°F. (750° - 550°), the convection heat transfer rate will be 200°F. ×65 BTU/hr. ft.$^2$ °F. = 13,000 BTU/hr. ft.$^2$. Additionally, radiation from the 850°F. catalyst surfaces to the 550°F. cooling surfaces will approximate 3,300 BTU/hr. ft.$^2$ resulting in a total of 16,300 BTU/hr. ft.$^2$. The total heat transfer cooling surface area required is 920,000 BTU/hr./16,300 BTU/hr. ft.$^2$ = 56,400 ft.$^2$. This area is realized by providing three vats of 1430, 2 inches diameter reaction tubes, each of which is 25 feet long.

Catalytically Coated Surface Area

The total required catalytic surface area is $$250,000,000 \text{ SCFD}/1470 \text{ SCFD/ft.}^2 = 170,000 \text{ ft.}^2$$

This will require an average 3 ft.$^2$ of catalytical surface area per ft.$^2$ of cooling surface. Trial and errror calculations indicate that this requirement can be met by making the first catalytic insert 46a 1.5, the second catalytic area 46b, 3.0, and the third catalytic area 46c, 4.5 ft.$^2$ of catalyst/ft.$^2$ of cooling surface.

The resultant design will consist of three vats 41a, 41b, 41c of 1500 2 inches I.D. reaction tubes 44, 25 feet long. The first vat 41a has catalytic inserts 46a with three fins (1.5 ft.$^2$/ft.$^2$). The second vat 41b has catalytic inserts 46b with 5 fins (3 ft.$^2$/ft.$^2$) and the last bank has catalytic inserts 46c with eight fins (4.5 ft$^2$/ft.$^2$). Each bank is immersed in boiling water at 1,000 psig. to produce process steam.

It is therefore seen that the degree of reactivity in each vat is based upon the ability to remove heat from the catalyst surfaces. That is, the degree of reactivity (SCF of synthetic gas produced per square foot of catalyst surfaces) times the heat effect in the reaction (BTU/SCF of synthetic gas produced) times the catalyst surface area per square foot of cooling area is equal to the heat removal rate in BTU/hr. per ft.$^2$ of cooling surface.

In summary, it should be clear from the operation of the process as described and from the series relationship of the methanator vats 41, that all the vats may be viewed in sum total as amounting to one enclosure having zones of different degrees of catalytic reactivity with the reactivity rate of the catalyst increasing in a predetermined manner as the feed gases progressively flow through the enclosure. More specifically, the degress of reactivity in each zone are stepped by increasing the area of the catalyst. However, the catalytic reactivity rate could also be stepped by using different catalysts having, as a function of their chemical composition, different degrees of reactivity.

Having thus defined our invention, it is apparent that several modifications of the methanator disclosed may appear obvious to one skilled in the art without departure from the spirit or essence of the invention. For example, only one methanator vat need be employed if the catalytic reactivity is progressively varied within the reaction tubes therein. While the methane reaction is shown taking place in tubes, other enclosure shapes may be employed so long as the catalytic and cooling area design parameters are met. While the methanator vats have been shown to be three in number, feed gas compositions can raise or lower the number of methanator vats employed. Alternatively, the feed gases, if desired, could be partially reacted in one or more of the methanator vats and conventional methanators such as fluidized beds could be employed to complete the reaction. Additionally, while the methanator has been shown to operate with a feed gas comprising reductants CO and $H_2$ to produce methane, the invention is capable of being operated to produce any type of product gas resulting from an exothermic reaction of the fed gases. It is our intention to include all such modifications and alternations insofar as they come within the scope of the present invention.

It is the essence of the invention to provide an enclosure for reacting reducing gases in the presence of catalysts having varying degrees of reactivity whereby the heat produced from the reaction within the enclosure is substantially dissipated by a cooling medium in heat transfer relationship with the enclosure.

We claim:

1. Apparatus for producing a synthetic gas from a feed gas in an exothermic reaction, said feed gas including reductants and synthetic gas, said apparatus comprising:
    a first methanator vat;
    a second methantor vat;
    a first plurality of elongated heat exchange enclosures disposed within said first methanator vat;
    a second plurality of elongated heat exchange enclosures disposed within said second methanator vat;
    each heat exchange enclosure having an open inlet end, an open outlet end and a constant cross-section;
    first conduit means connecting said feed gas to said inlet ends of said first plurality of heat exchange enclosures;
    second conduit means connecting said outlet end of said first plurality of heat exchange enclosures with said inlet ends of said second plurality of heat exchange enclosures for transmitting said feed gas from said first plurality of heat exchange enclosures to said second plurality of heat exchange enclosures;
    means for feeding said feed gas through said first conduit means at a temperature sufficient to react said reductants in an exothermic reaction and at a pressure sufficient to carry said feed gas through said first and second heat exchange enclosures at a predetermined velocity to produce said synthetic gas;
    first catalytic insert means disposed within said first plurality of heat exchange enclosures dividing each enclosure into a plurality of ducts and having a first degree of reacitivity effective when said feed gas is contacted therewith to generate a generally constant quantity of heat throughout the length of said first plurality of heat exchange enclosures;
    second catalytic insert means disposed within said second plurality of heat exchange enclosures dividing each second enclosure into a plurality of ducts and having a second degree of reactivity higher than said first degree of reactivity effective when said feed gas is contacted therewith to generate a generally constant quantity of heat throughout the length of said second plurality of heat exchange enclosures;
    cooling means disposed only within each methanator vat and including a liquid surrounding the exterior of each heat exchange enclosure for dissipating a significant portion of said heat generated in said exothermic reaction.

2. Apparatus of claim 1 wherein:
    a first insert member coated with a catalytic substance and removably suspended within each heat exchanger enclosure in said first plurality of heat exchange enclosures defines said first catalytic insert means;
    a second insert member coated with a catalytic substance and removably suspended within each heat exchange enclosure in said second plurality of heat exchange enclosures defines said second catalytic insert means; and
    said first and second catalytic insert means and said cooling means are effective to prevent the temperature of said feed gas in each heat exchange enclosure from rising to a temperature whereat said catalytic substance would be destroyed.

3. Apparatus of claim 1 wherein said first insert member is defined by a first configuration producing said first degree of reactivity and said second insert member is defined by a second configuration producing said second degree of reactivity, each configuration dividing each heat exchange enclosure into a plurality of longitudinally-extending ducts, each duct having a cross-sectional periphery including a portion of said enclosure and a portion of said insert member, the ratios of the areas of said enclosure portion and said insert member portion being constant for each duct.

4. Apparatus of claim 3 further including
a third vat containing a third plurality of heat exchange enclosures having catalytic inserts therein of a third degree of reactivity, higher than said second degree;
said feed means effective to direct said feed gases through said first, second and third pluralities of heat exchange enclosures;
a fourth vat containing a fourth plurality of heat exchange enclosures having catalytic inserts therein of said third degree of reactivity; and
valving means effective when said first, second and third catalytic insert members drop in reactivity to a predetemined value to cycle the flow of feed gas to said second, third and fourth pluralities of heat exhcange enclosures in series relationship.

5. A process for producing a synthetic gas from a feed gas containing reductants and synthetic gas in a preferred ratio to one another which react together in an exothermic reaction to produce said synthetic gas, said process comprising the steps of:
flowing said feed gas at a predetermined temperature and pressure through a first plurality of reaction tubes containing catalytic inserts having a first degree of reactivity and submersed in a first vat containing a liquid cooling medium to define a first zone;
flowing said feed gas through a second plurality of reaction tubes containing catalytic inserts having a second degree of reactivity higher than said first degree of reactivity and submersed in a second vat containing a liquid cooling medium to define a second zone;
subdividing the flow of said feed gas into individual units of mass flowing through ducts formed in each reaction tube by said catalytic inserts and contacting each unit of mass flow of said feed gas in each duct to a constant catalytic insert area and to a constant reaction tube area;
partially reacting said feed gas in said first zone to generate heat at a controlled rate while generally dissipating all the heat produced in said first zone by said liquid cooling medium in said first vat being in contact with exterior of said first plurality of reaction tubes;
continuing to react said feed gas in said second zone to generate heat at a controlled rate while generally dissipating all the heat produced in said second zone by said liquid cooling medium in said second vat being in contact with the exterior of said second plurality of reaction tubes.

6. The process of claim 5 further including
flowing said feed gas through a third plurality of tubes having catalytic inserts with a third degree of reactivity higher than said second degree of reactivity and submersed in a vat containing a liquid cooling medium;
providing a fourth plurality of tubes having catalytic inserts of said third degree of reactivity and submersed in a vat containing a liquid cooling medium; and
cycling said flow of feed gas from said first, second and third tube pluralities, in series, to said second, third and fourth tube pluralities when the percentage of synthetic gas in the product gas leaving said third tubes drops below a predetermined value.

7. In a process for producing methane from coal including the steps of gasifying the coal to produce gaseous product in a solid gasifier, cleansing said gaseous products, passing said gaseous products through a shift converter to produce a feed gas generally comprised of CO and $H_2$ in predetermined proportions and $CH_4$, the improvement comprising the steps of:
passing the feed gas at an elevated temperature and a relatively constant pressure through a first plurality of reaction tubes, each reaction tube containing a first catalytic insert having a first reactivity rate and dividing the reaction tube into a plurality of ducts;
reacting a first portion of the CO and $H_2$ feed gas constituents in the presence of said first catalytic insert to produce a partially reacted feed gas containing $CH_4$ in an exothermic reaction;
cooling the exterior of said first reaction tube by a liquid medium to remove a major portion of the heat produced in said exothermic reaction;
passing the partially reacted feed gas at an elevated temperature and relatively constant pressure through a second plurality of reaction tubes, each second reaction tube containing a second catalytic insert having a second reactivity rate greater than said first reactivity rate and dividing the second reaction tube into a plurality of ducts;
reacting a second portion of the CO and $H_2$ constituents in said partially reacted feed gas in the presence of said second catalytic insert to produce $CH_4$ is an exothermic reaction; and
cooling the exterior of said second reaction tube by a liquid medium to remove a major portion of the heat produced in said exothermic reaction.

8. The process of claim 7 further including the steps of
subdividing the flow of said feed gas into individual units of mass flowing through said ducts and each duct having a portion of its periphery defined to include a portion of the periphery of said reaction tube and a portion of said catalytic insert;
contacting each mass unit of feed gas flow with a constant catalytic insert area and a constant reaction tube area for all ducts in said first reaction tube; and
contacting each mass unit of partially reacted feed gas flow with a constant catalytic insert area and a constant reaction tube area for all ducts in said second reaction tube.

9. The process of claim 8 further including the step of passing said feed gas through said first and second plurality of reaction tubes solely by virtue of the pressure developed in said gasifier.

* * * * *

UNITED STATES PATENT AND TRADEMARK OFFICE
CERTIFICATE OF CORRECTION

PATENT NO. : 3,970,435
DATED : July 20, 1976
INVENTOR(S) : Thomas J. Schultz and Klaus H. Hemsath It is certified that error appears in the above-identified patent and that said Letters Patent are hereby corrected as shown below:

Column 1, line 57, change "fed" to -- feed --.
Column 3, line 40, change "physiical" to -- physical --.
Column 4, line 58, add -- 40 -- after "methanation reactor".
Column 5, line 2, change "seriies" to -- series --; line 56, change "inert" to -- insert --.
Column 6, line 18, change "metane" to -- methane --.
Column 7, line 28, change "H$_2$)" to -- H$_2$O --.
Column 8, line 34, add -- ) -- after "850°F"; line 38, change "connection" to -- convection --; line 43, change "30,000 lb./hr. ft." to -- 30,000 lb./hr. ft.$^2$ --.
Column 9, line 28, change "gress" to -- grees --; line 53, change "fed" to -- feed --; line 55, change "alternations" to -- alterations --.
Column 10, line 50, change "exchanger" to -- exchange --.
Column 11, line 19, change "gas" to -- gases --; line 21, change "exhcange" to -- exchange --.
Column 12, line 39, change "is" to -- in --.

Signed and Sealed this

Twenty-eighth Day of September 1976

[SEAL]

Attest:

RUTH C. MASON
Attesting Officer

C. MARSHALL DANN
Commissioner of Patents and Trademarks